United States Patent

Doria et al.

[11] Patent Number: 5,352,676
[45] Date of Patent: Oct. 4, 1994

[54] MORPHALINOMETHYL-SUBSTITUTED 1-PHENYL-INDERO-[1,2-C]PYRAZOL-3-YL DERIVATIVES OF 2-CYANO-3-OXO-PROPANAMIDES USEFUL IN THE TREATMENT OF RHEUMATOID ARTHRITIS

[75] Inventors: Gianfederico Doria, Milan; Anna M. Isetta, Rho; Rinaldo Ferreccio, Gorgonzola; Mario Ferrari, Milan; Maria C. Fornasiero, Vigevano; Domenico Trizio, Cassina Rizzardi, all of Italy

[73] Assignee: Farmitalia Carlo Erba Srl, Milan, Italy

[21] Appl. No.: 84,470

[22] Filed: Jul. 1, 1993

Related U.S. Application Data

[62] Division of Ser. No. 972,391, Nov. 6, 1992, Pat. No. 5,260,328, which is a division of Ser. No. 613,482, Oct. 31, 1990, Pat. No. 5,196,445.

[30] Foreign Application Priority Data

Apr. 6, 1989 [GB] United Kingdom ....... GB 8907799.4
Apr. 4, 1990 [WO] PCT Int'l Appl. .......... PCT/EP90/00527

[51] Int. Cl.5 .................. A61K 31/535; A61K 31/115
[52] U.S. Cl. .................. 514/237.5; 514/405; 514/825
[58] Field of Search ...................... 514/405, 237.5, 825

[56] References Cited

U.S. PATENT DOCUMENTS

| 4,173,634 | 11/1979 | Kuapcho | 424/248.4 |
| 4,268,516 | 5/1981 | Lombardino | 424/273 |
| 4,415,569 | 11/1983 | Yasuo | 424/248.57 |

FOREIGN PATENT DOCUMENTS

| 0274443 | 7/1988 | European Pat. Off. . |
| 0278603 | 8/1988 | European Pat. Off. . |
| 0347773 | 12/1989 | European Pat. Off. . |
| 89/12638 | 12/1989 | PCT Int'l Appl. . |
| WO90/01481 | 2/1990 | PCT Int'l Appl. . |
| 22227741 | 8/1990 | United Kingdom . |

OTHER PUBLICATIONS

Jürgen Drews, "Immunpharmakologie", 1986, Springer-Verlag, (Berlin DE), pp. 71–73.
The Merck Manual of Diagnosis and Therapy, 15th edition, 1987, Merck Sharp & Dohme Research Laboratories, (Rahway, N.J., US), pp. 319–322.

*Primary Examiner*—Gregory Hook
*Attorney, Agent, or Firm*—Nikaido, Marmelstein, Murray & Oram

[57] ABSTRACT

This invention relates to a method of treating rheumatoid arthritis, which method comprises administering to a mammal a therapeutically effective amount of a compound of formula (I):

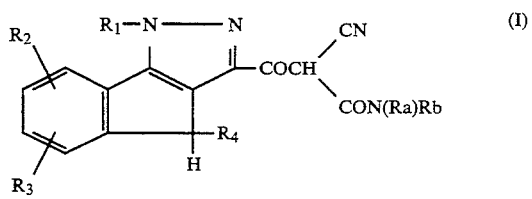

wherein
$R_1$ is unsubstituted or substituted phenyl;
$R_2$ is a morpholinomethyl group;
$R_3$ is hydrogen;
$R_4$ is hydrogen or $C_1$-$C_6$ alkyl;
$R_a$ is hydrogen; and
$R_b$ is a group —$(A)_m$—$R_5$ wherein m is zero or 1, A is a $C_1$-$C_6$ alkylene chain and $R_5$ is unsubstituted or substituted phenyl;
or a pharmaceutically acceptable salt thereof.

2 Claims, No Drawings

MORPHALINOMETHYL-SUBSTITUTED 1-PHENYL-INDERO-[1,2-C]PYRAZOL-3-YL DERIVATIVES OF 2-CYANO-3-OXO-PROPANAMIDES USEFUL IN THE TREATMENT OF RHEUMATOID ARTHRITIS

This is a division of application Ser. No. 07/972,391 filed Nov. 6, 1992, now U.S. Pat. No. 5,260,328, which is a division of application Ser. No. 07/613,482 filed Oct. 31, 1990, now U.S. Pat. No. 5,196,445.

This invention relates to the treatment of rheumatoid arthritis and other autoimmune diseases.

Cell-mediated autoimmune disease is a debilitating condition which results when the immune system attacks autologous tissue. One consequence of autoimmunity is that insoluble antigen-antibody immune complexes are deposited in tissues and chemotactic factors attract phagocytic cells, such as macrophages and/or leukocytes, for the removal of this material.

During phagocytosis these activated cells release a number of enzymes, including collagenase and lysosomal enzymes, which act indiscriminately in destroying extracellular collagen fibers of the affected tissue. In the case of the rheumatoid arthritis, for example, this process ultimately results in destruction of connective tissue surrounding the joints.

Furthermore, activated macrophages are known to produce and release proinflammatory substances, such as the monokines IL-1 and TNF besides prostaglandins, which contribute to extend and exacerbate the pathologic course of the disease.

From these considerations the current use of immunosuppressive agents appears justified in the therapeutic treatment of the autoimmune disorders. The primary aim of such a treatment is to depress the activity of the immune cells in order to improve the course of the disease.

In EP-A-0274443. PCT/EP89/00683, PCT/EP89/00682 and British Patent Application 8902596.9 we have described compounds endowed with an immunomodulating activity, which are used in particular as immunostimulating agents by virtue of their effectiveness in the stimulation of macrophage activity.

Surprisingly, we have now found that the compounds described in the above mentioned patent applications, herein defined as compounds of formula (I), and their salts are useful in the therapeutic treatment of rheumatoid arthritis and other autoimmune diseases in mammals, including humans.

This finding is unexpected. Any compound effective in stimulating the activity of the macrophages, immune cells which contribute directly, as specified above, to the pathology of the autoimmune disorders, would be expected to cause adverse effects when used in the active therapy for these diseases. In effect macrophage stimulation results in an increase of the release of proteolytic and lysosomal enzymes as well as monokines, and therefore should exacerbate the progressive destruction of the affected tissue.

Furthermore it is well known that immunosuppressive agents, currently used in the treatment of the autoimmune diseases, are cytotoxic and are not suitable for long term therapy because they heavily debilitate the body's natural defence mechanism.

Conversely, our compounds of formula (I), which are surprisingly useful in the treatment of the autoimmune disorders, are devoid of the negative features common to immunosuppressive agents in virtue of their immunostimulating activity.

By consequence, they have to be considered a new significant improvement in an effective and safe therapy for the rheumatoid arthritis and other autoimmune diseases.

The present invention relates in one aspect to a method of treatment of autoimmune diseases by administering to mammals, including humans, in need of such treatment, a therapeutically effective amount of an active heteroaryl-3-oxo-propanenitrile derivative of formula (I), as herein defined, or a pharmaceutically acceptable salt thereof.

In another aspect, this invention relates to the use of a heteroaryl-3-oxo-propanenitrile derivative of formula (I), as herein defined, or a pharmaceutically acceptable salt thereof in the preparation of a pharmaceutical composition useful for treating autoimmune diseases in mammals, including humans.

Examples of autoimmune diseases which can be treated by the compound of formula (I), or the pharmaceutical compositions containing them, according to the method of treatment of the present invention, are rheumatoid arthritis, systemic lupus erythematosus, juvenile diabetes, autoimmune haemolytic anaemia, ulcerative colitis, idiopathic thrombocytopenic purpura, active chronic hepatitis, glomerulonephritis, multiple sclerosis, idiopathic leucopenia, primary biliary cirrhosis, thyroiditis, thyrotoxicosis, dermatomyositis, discoid lupus erythematosus, psoriasis, psoriatic arthritis, regional enteritis, nephrotic syndrome, lupus nephritis, lupoid hepatitis, Sjögren's syndrome, Goodpasture's syndrome, Wegener's granulomatosis, scleroderma, Sezary's disease, uveitis and mumps orchitis.

In particularr, preferred examples of autoimmune diseases which can be treated by the compounds of formula (I), or the pharmaceutical composition containing them, according to the method of treatment of the present invention, are rheumatoid arthritis, systemic lupus erythematosus, juvenile diabetes, autoimmune haemolytic anaemia, ulcerative colitis, idiopathic thrombocytopenic purpura, active chronic hepatitis, glomerulonephritis and multiple sclerosis.

The heteroaryl-3-oxo-propanenitrile derivatives, which are effective in stimulating macrophage activity and are useful in the method of treatment, or in the preparation of the pharmaceutical compositions, according to the present invention, are described in our patent application EP-A-0274443, PCT/EP89/00683, PCT/EP89/00682 and British patent application No. 8902596.9, and can be represented by the following formula (I).

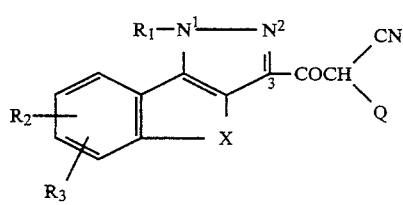

wherein

X represents:

a) an oxygen atom or a —S(O)$_n$—group, wherein n is zero, 1 or 2;
b) a —CH(R$_4$)—group, wherein R$_4$ represents hydrogen or C$_1$-C$_6$ alkyl;
c) an

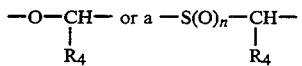

group, wherein n and R$_4$ are as defined above;
d) a

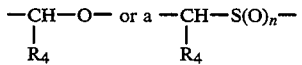

group, wherein n and R$_4$ are as defined above; or
e) a

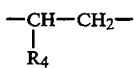

group, wherein R$_4$ is as defined above;
R$_1$ represents C$_1$-C$_6$ alkyl, pyridyl or phenyl, the phenyl being unsubstituted or substituted by one or two substituents chosen independently from halogen, trifluoromethyl, C$_1$-C$_6$ alkyl, C$_1$-C$_6$ alkoxy, nitro, amino, formylamino and C$_2$-C$_8$ alkanoylamino;
R$_2$ represents:
a) hydrogen, halogen or C$_1$-C$_6$ alkyl;
b) hydroxy, C$_1$-C$_6$ alkoxy or C$_3$ or C$_4$ alkenyloxy;
c) nitro, amino, formylamino or C$_2$-C$_8$ alkanoylamino;
d) di (C$_1$-C$_6$ alkyl) amino or a

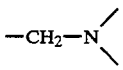

group wherein each of R' and R" independently is C$_1$-C$_6$ alkyl or R' and R", taken together with the nitrogen atom to which they are linked, form a heterocyclic ring which is selected from N-pyrrolidinyl, N-piperazinyl, hexahydroazepin-1-yl, thiomorpholino, morpholino and piperidino and which is unsubstituted or substituted by C$_1$-C$_6$ alkyl;
e) —CH$_2$OH,—CHO,—COOH or C$_2$-C$_7$ alkoxycarbonyl;
f) a

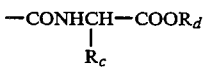

group wherein R$_d$ is hydrogen or C$_1$-C$_6$ alkyl and R$_c$ is hydrogen, phenyl or the side-chain of an α-aminoacid;
g) a

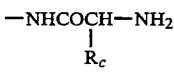

group, wherein R$_c$ is as defined above;
h) a

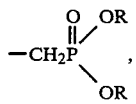

a —CH$_2$OCO(CH$_2$)$_n$COOR or a —NHCO(CH$_2$)$_n$COOR group, wherein n is as defined above and R is hydrogen or C$_1$-C$_6$alkyl;
k) a —CH=N—OR'$_1$ group wherein R'$_1$ is hydrogen or a —CH$_2$COOH group;
i) a —CH=N—NH—R'$_2$ group wherein R'$_2$ is hydrogen, —CH$_2$CH$_2$OH, C$_2$ or C$_3$ alkoxycarbonyl or a —(CH$_2$)$_p$-R'$_3$ group wherein p is 1 or 2 and R'$_3$ is COOH or C$_2$—C$_7$ alkoxycarbonyl;
l) a

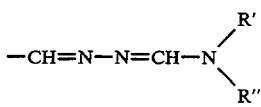

group wherein R' and R" are as defined above; or
m) a

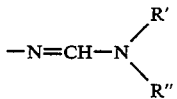

group wherein R' and R" are as defined above;
n) a C$_2$-C$_7$ alkoxycarbonyl group substituted by a

group, wherein R' and R" are as defined above;
R$_3$ is as R$_2$ defined above under a), b), and c);
Q represents hydrogen, carboxy, C$_2$-C$_7$ alkoxycarbonyl or a

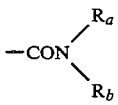

group wherein R$_a$ represents hydrogen or C$_1$-C$_{20}$ alkyl and R$_b$ represents C$_1$-C$_{20}$ alkyl, a

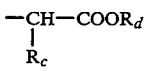

group wherein R$_d$ and R$_c$ are as defined above or a —(A)$_m$—R$_5$ group wherein m is zero or 1, A is a C$_1$-C$_6$ alkylene chain and R$_5$ is
a') C$_5$-C$_8$ cycloalkyl;
b') pyridyl, unsubstituted or substituted by one or two substituents chosen independently from halogen, C$_1$-C$_6$ alkyl and C$_1$-C$_6$ alkoxy;
c') phenyl, unsubstituted or substituted by one or two substituents independently chosen from halogen, CF$_3$, C$_1$-C$_6$ alkyl, C$_1$-C$_6$ alkoxy, amino, nitro, formylamino, $C_2-C_8$ alkanoylamino, di($C_1-C_6$ alkyl)-amino, hydroxy, formuloxy and $C_2-C_8$ alkanoyloxy;

d') phenyl substituted by a —CH$_2$OH, COOH, $C_2-C_7$ alkoxycarbonyl or a

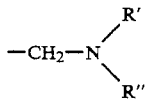

group wherein R' and R" are as defined above and optionally by another substituent chosen from halogen, $C_1-C_6$alkyl, $C_1-C_6$ alkoxy, amino, nitro, formylamino, $C_2-C_8$ alkanoylamino, hydroxy, formyloxy and $C_2-C_8$ alkanoyloxy, or e') 2-thienyl, 2-furyl or 1-($C_1-C_6$ alkyl)-pyrrol-2-yl; or f') a heterocyclic ring which is selected from 2-pyrimidyl; 2-thiazolyl and 3-isoxazolyl and which is unsubstituted or substituted by $C_1-C_6$ alkyl.

It has to be noticed that the compounds of formula (I) may be represented also by a tautomeric structure, namely the enol structure of formula (Ia)

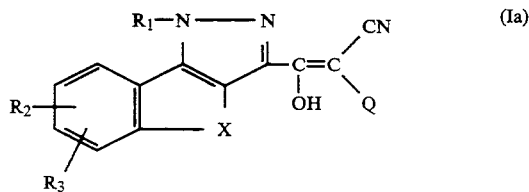

wherein X, R$_1$, R$_2$, R$_3$ and Q are as defined above. However, the compounds of formula (Ia), which fall within the scope of the present invention too, are described in the present specification as compounds of formula (I).

A halogen atom is preferably chlorine or fluorine.

The alkyl, alkylene, alkanoyloxy, alkoxy and alkanoylamino groups may be branched or straight chain groups.

A $C_1-C_{20}$ alkyl group is preferably a $C_1-C_{10}$ alkyl group, for example a $C_1-C_6$ alkyl group. A $C_1-C_6$ alkyl group is, e.g., methyl, ethyl, propyl, isopropyl, butyl or tert.butyl. A $C_1-C_4$ alkyl group is more preferred such as methyl, ethyl or tert.butyl.

A C$_3$ or C$_4$ alkenyloxy group is preferably allyloxy.

A $C_1-C_6$ alkoxy group is, e.g., methoxy, ethoxy, propoxy, isopropoxy, butoxy or tert.butoxy. Preferably it is a $C_1-C_4$ alkoxy group such as methoxy, ethoxy or propoxy.

A $C_5-C_8$ cycloalkyl group is preferably cyclopentyl or cyclohexyl.

A $C_2-C_8$ alkanoylamino group is preferably a $C_2-C_6$ alkanoylamino group, for example a $C_2-C_4$ alkanoylamino group such as acetylamino or propionylamino. A $C_2-C_8$ alkanoyloxy group is preferably a $C_2-C_6$ alkanoyloxy group, for example a $C_2-C_4$ alkanoyloxy group such as acetoxy or propionyloxy.

A $C_2-C_7$ alkoxycarbonyl group is preferably a $C_4-C_7$ alkoxycarbonyl group, in particular a tertiary $C_4-C_7$ alkoxycarbonyl group such as tert.butoxycarbonyl or tert.amyloxycarbonyl.

A $C_1-C_6$ alkylene chain is preferably a $C_1-C_3$ alkylene chain, such as a —CH$_2$—, —(CH$_2$)$_2$—, —(CH$_2$)$_3$—,

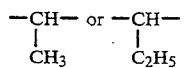

chain.

A di($C_1-C_6$ alkyl)amino group is preferably a di($C_1-C_4$ alkyl)amino group, in particular a di($C_1$ or $C_2$ alkyl)amino group.

A

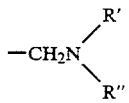

group, wherein R' and R" taken together with the nitrogen atom form a heterocyclic ring, is preferably a morpholinomethyl, a thiomorpholinomethyl or a N-piperazinyl-methyl group, wherein said heterocyclic rings may be unsubstituted or substituted by $C_1-C_4$ alkyl.

The asymmetric carbon atom to which the R$_c$ group is linked may have either the R or S configuration. The side-chain of an α-aminoacid is specifically the residue obtained from an α-aminoacid by removing the amino and the carboxy groups together with the α-carbon atom to which they are linked. The side-chain of an α-aminoacid as defined above is preferably the side-chain deriving from a naturally occurring aminoacid.

Examples of such aminoacids are alanine, valine, leucine, isoleucine, phenylalanine, proline, hydroxyproline, serine, threonine, cysteine, cystine, methionine, tryptophan, tyrosine, asparagine, glutamine, aspartic acid, glutamic acid, lysine, arginine, histidine and phenylserine. Preferred examples of said chains of the above mentioned aminoacids are —CH$_3$ (deriving from alanine), —CH$_2$—CH(CH$_3$)$_2$ (deriving from leucine) and —CH$_2$—C$_6$H$_5$ (deriving from phenylalanine).

Examples of pharmaceutically acceptable salts of the compounds of formula (I) are either those with inorganic bases, such as sodium, potassium, calcium and aluminium hydroxides, or with organic bases, such as lysine, triethylamine, triethanolamine, dibenzylamine, methylbenzylamine, di-(2-ethyl-hexyl)-amine, piperidine, N-ethylpiperidine, N,N-diethylaminoethylamine, N-ethylmorpholine, β-phenethylamine, N-benzyl-β-phenethylamine, N-benzyl-N,N-dimethylamine and the other acceptable organic amines, as well as the salts with inorganic, e.g. hydrochloric, hydrobromic and sulphuric acids and with organic acids, e.g. citric, tartaric, maleic, malic, fumaric, methanesulphonic and ethanesulphonic acids. Preferred salts of the compounds of formula (I) are the sodium and the potassium salts thereof.

Suitable compounds of formula (I) for use in the invention include in particular the following compounds which are described in our above identified European, British and international patent applications:

2-cyano-3-(1,4-dihydro-1-phenyl-[1]-benzothiopyrano[4,3-c]pyrazol-3-yl)-3-oxo-N-phenyl-propanamide;

N-benzyl-2-cyano-3-(1,4-dihydro-1-phenyl-[1]-benzothiopyrano [4,3-c]pyrazol-3-yl)-3-oxo-propanamide;

2-cyano-N-(4-fluoro-phenyl)-3-(1,4-dihydro-1-phenyl-[1]benzothiopyrano[4,3-c]pyrazol-3-yl)-3-oxo-propanamide;

2-cyano-N-(4-fluoro-phenyl)-3-[1-(4-fluoro-phenyl)-1,4-dihydro-[1]-benzothiopyrano[4,3-c]pyrazol-3-yl]-3-oxo-propanamide;

2-cyano-3-(1,4-dihydro-8-methyl-1-phenyl-[1]-benzothiopyrano [4,3-c]pyrazol-3-yl)-3-oxo-N-phenyl-propanamide;

3-(8-chloro-1,4-dihydro-1-phenyl-[1]-benzothiopyrano[4,3-c]pyrazol-3-yl)-2-cyano-3-oxo-N-phenyl-propanamide;

3-(6-amino-1,4-dihydro-1-phenyl-[1]-benzothiopyrano[4,3-c]pyrazol-3-yl)-2-cyano-3-oxo-N-phenyl-propanamide;

N-(3-chloro-phenyl)-2-cyano-3-(1,4-dihydro-1-phenyl-[1]benzothiopyrano[4,3-c]pyrazol-3-yl)-3-oxo-propanamide;

2-cyano-3-(1,5-dihydro-1-phenyl-[2]-benzothiopyrano[4,3-c]pyrazol-3-yl)-3-oxo-N-phenyl-propanamide;

2-cyano-3-(4,5-dihydro-1-phenyl-[1]-benz[g]indazol-3-yl)-3-oxo-N-phenyl-propanamide;

2-cyano-3-(8-ethoxalylamino-1,4-dihydro-1-phenyl-[1]-benzothiopyrano[4,3-c]pyrazol-3-yl)-3-oxo-N-phenyl-propanamide;

2-cyano-3-(1,4-dihydro-1-phenyl-[1]-benzothiopyrano[4,3-c]pyrazol-3-yl)-N-(3-nitro-phenyl)-3-oxo-propanamide;

2-cyano-3-(1,4-dihydro-1-phenyl-[1]-benzothiopyrano[4,3-c]pyrazol-3-yl)-3-oxo-N-(3-trifluoromethyl-phenyl)-propanamide;

3-(7-tert.butyl-1,4-dihydro-1-phenyl-indeno[1,2-c]pyrazol-3-yl)-2-cyano-3-oxo-N-phenyl-propanamide;

2-cyano-3-(7-fluoro-1,4-dihydro-1-phenyl-indeno[1,2-c]pyrazol-3-yl)-3-oxo-N-phenyl-propanamide;

2-cyano-N-(4-fluoro-phenyl)-3-(7-fluoro-1,4-dihydro-1-phenyl-indeno[1,2-c]pyrazol-3-yl-3-oxo-propanamide;

2-cyano-N-(4-fluoro-phenyl)-3-(1,4-dihydro-7-methyl-1-phenyl-indeno[1,2-c]pyrazol-3-yl)-3-oxo-propanamide;

3-(6-tert.butoxycarbonyl-1,4-dihydro-1-phenyl-[1]-benzothiopyrano[4,3-c]pyrazol-3-yl)-2-cyano-3-oxo-N-phenyl-propanamide;

3-(5-tert.butoxycarbonyl-1,4-dihydro-1-phenyl-indeno[1,2-c]pyrazol-3-yl)-2-cyano-3-oxo-N-phenyl-propanamide;

2-cyano-3-(1,4-dihydro-7-morpholinomethyl-1-phenyl-indeno[1,2-c]pyrazol-3-yl)-3-oxo-N-phenyl-propanamide;

2-cyano-3-(1,4-dihydro-5-morpholinomethyl-1-phenyl-indeno [1,2-c]pyrazol-3-yl)-3-oxo-N-phenyl-propanamide;

2-cyano-3-(8-fluoro-1,4-dihydro-6-morpholinomethyl-1-phenyl-[1]-benzopyrano[4,3-c]pyrazol-3-yl)-3-oxo-N-phenyl-propanamide;

2-cyano-3-(1,4-dihydro-8-morpholinomethyl-1-phenyl-[1]benzo-pyrano[4,3-c]pyrazol-3-yl)-3-oxo-N-phenyl-propanamide;

2-cyano-3-(1,4-dihydro-6-N,N-dimethylaminoethoxycarbonyl-1-phenyl-[1]-benzothiopyrano[4,3-c]pyrazol-3-yl)-3-oxo-N-phenyl-propanamide;

3-(6-caroboxy-1,4-dihydro-1-phenyl-[1]-benzothiopyrano [4,3-c]pyrazol-3-yl)-2-cyano-3-oxo-N-phenyl-propanamide;

3-(5-carboxy-1,4-dihydro-1-phenyl-indeno[1,2-c]pyrazol-3-yl)-2-cyano-3-oxo-N-phenyl-propanamide;

2-cyano-3-(1,4-dihydro-1-phenyl-indeno[1,2-c]pyrazol-3-yl)-3-oxo-N-phenyl-propanamide;

2-cyano-N-(4-fluoro-phenyl)-3-[1-(4-fluoro-phenyl)-1,4-dihydro-indeno[1,2-c]pyrazol-3-yl]-3-oxo-propanamide;

2-cyano-N-(4-fluoro-phenyl)-3-(1,4-dihydro-1-phenyl-indeno[1,2-c]pyrazol-3-yl)-3-oxo-propanamide;

N-(3-chloro-phenyl)-2-cyano-3-(1,4-dihydro-1-phenyl-indeno[1,2-c]pyrazol-3-yl)-3-oxo-propanamide;

2-cyano-3-(1,4-dihydro-7-methyl-1-phenyl-indeno[1,2-c]pyrazol-3-yl)-3-oxo-N-phenyl-propanamide;

2-cyano-3-oxo-(1-phenyl-1H-benzothieno[3,2-c]pyrazol-3-yl)-N-phenyl-propanamide;

3-(8-carboxy-1,4-dihydro-1-phenyl-[1]-benzopyrano[4,3-c]pyrazol-3-yl)-2-cyano-3-oxo-N-phenyl-propanamide;

2-cyano-3-(1,4-dihydro-1-phenyl-[1]-benzopyrano[4,3-c]pyrazol-3-yl)-3-oxo-N-phenyl-propanamide;

3-(8-amino-1,4-dihydro-1-phenyl-[1]-benzothiopyrano[4,3-c]pyrazol-3-yl)-2-cyano-3-oxo-N-phenyl-propanamide;

and the pharmaceutically acceptable salts thereof, in particular the sodium and the potassium salts.

The compounds of formula (I) and the salts thereof can be prepared by a process comprising:

a) reacting a compound of formula (II)

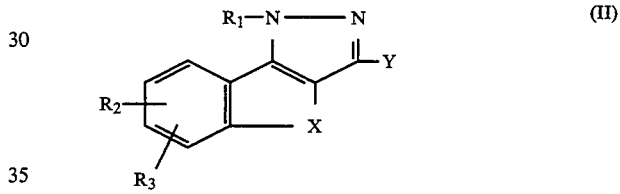

wherein

X, R₁, R₂ and R₃ are as defined above and Y is carboxy or a reactive derivative of a carboxy group, with a compound of formula (III)

wherein

Q' is as Q defined above, except carboxy, so obtaining a compound of formula (I), wherein Q is as defined above except carboxy; or b) reacting a compound of formula (IV)

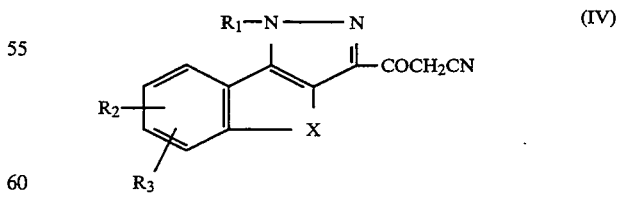

wherein

X, R₁, R₂ and R₃ are as defined above, with a compound formula (V)

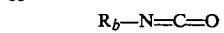

wherein $R_b$ is as defined above, so obtaining a compound of formula (I) wherein Q is a —CONHR$_b$ group, wherein R$_b$ is as defined above; or c) reacting a compound of formula (VI)

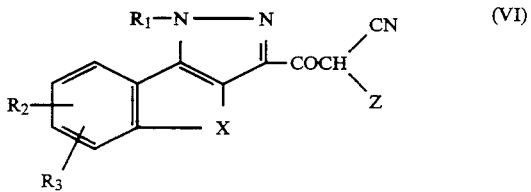

wherein

X, R$_1$, R$_2$ and R$_3$ are as defined above and Z is a reactive derivative of a carboxy group, with a compound of formula (VII)

wherein

R$_a$ and R$_b$ are as defined above, so obtaining a compound of formula (I) wherein Q is a

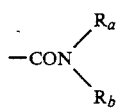

group, wherein R$_a$ and R$_b$ are as defined above; or d) hydrolysing a compound of formula (I), wherein Q is a C$_2$–C$_7$ alkoxycarbonyl or

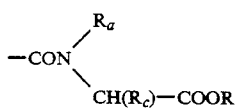

group in which R$_a$ and R$_c$ are as defined above and R is C$_1$–C$_6$ alkyl, so as to obtain the corresponding compound of formula (I), wherein Q is a free carboxy group or a

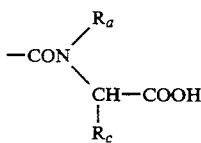

group, in which R$_a$ and R$_c$ are as defined above; and, if desired, converting a compound of formula (I) into another compound of formula (I) and/or, if desired, converting a compound of formula (I) into a pharmaceutically acceptable salt and/or, if desired, converting a salt into a free compound, and/or, if desired, separating a mixture of isomers of a compound of formula (I), into the single isomers.

The details inherent the methods of preparation are described in the above-identified European, International and British patent applications, the disclosures of which are incorporated herein by reference. Surprisingly, as stressed above, we have now found that the compounds of formula (I), here above described, and their salts are useful in the therapeutic treatment in mammals, including humans, of the autoimmune diseases, such as the herebelow specified ones: rheumatoid arthritis, systemic lupus erythematosus, juvenile diabetes, autoimmune haemolytic anaemia, ulcerative colitis, idiopathic thrombocytopenic purpura, active chronic hepatitis, glomerulonephritis, multiple sclerosis, idiopathic leucopenia, primary biliary cirrhosis, thyroiditis, thyrotoxicosis, dermatomyositis, discoid lupus erythematosus, psoriasis, psoriatic arthritis, regional enteritis, nephrotic syndrome, lupus nephritis, lupoid hepatitis, Sjögren's syndrome, Goodpasture's syndrome, Wegener's granulomatosis, scleroderma, Sezary's disease, uveitis and mumps orchitis.

The above specified therapeutical activity of the compounds of formula (I) is proved, for example, by the fact that they are active in the following biological test in vivo: test of Myco bacterium Smeqmatis induced adjuvant arthritis in rats, as described in the experimental part.

In view of their high biological activity and low toxicity the compounds of the invention can be safely used in medicine. For example, the approximate acute toxicity (LD$_{50}$) in the mouse of the compounds 2-cyano-3-(1,4-dihydro-1-phenyl-[1]-benzopyrano[4,3-c]pyrazol-3-yl)-3-oxo-N-phenyl-propanamide, and 2-cyano-3-(1,4-dihydro-1-phenyl-[1]-benzothiopyrano[4,3-c]pyrazol-3-yl)-3-oxo-N-phenyl-propanamide, determined per os with single administration of increasing doses and measured on the seventh day after the day of treatment, is higher than 800 mg/kg. Analogous toxocity data have been found for the other compounds of the invention.

The therapeutic regimen for the different clinical syndromes must be adapted to the type of pathology taking into account, as usual, also the route of administration, the form in which the compound is administered and the age, weight and conditions of the subject involved.

The oral route is employed, in general, for all conditions requiring such compounds. Preference is given to intravenous injection or infusion for the treatment of acute syndromes. For maintenance regimens the oral or parenteral, e.g. intramuscular or subcutaneous, route is preferred.

For these purposes the compounds of the invention for example 2-cyano-3-(1,4-dihydro-1-phenyl-[1]-benzothiopyrano[4,3-c]pyrazol-3-yl)-3-oxo-N-phenyl-propanamide (internal code FCE 24578) and 2-cyano-3-(1,4-dihydro-1-phenyl-indeno[1,2-c]pyrazol-3-yl)-3-oxo-N-phenyl-propanamide (internal code FCE 25276), can be administered orally at doses ranging e.g. from about 0.5 to about 10 mg/kg of body weight per day in adult humans. Doses of active compounds ranging e.g. from about 0.2 to about 5 mg/kg of body weight can be used for the parenteral administration in adult humans. Of course, these dosage regimens may be adjusted to provide the optimal therapeutic response. The present invention also refers, in another aspect, to the pharmaceutical compositions suitable for the treatment of the autoimmune diseases in mammals, comprising a compound of formula (I), as defined above, in association with a pharmaceutically acceptable excipient (which can be a carrier or diluent).

The nature of the pharmaceutical compositions containing the compounds of formula (I) in association with pharmaceutically acceptable carriers or diluents will, of course, depend upon the desired route of administration. The compositions may be formulated in the conventional manner with the usual ingredients. For example, the compounds of the invention may be administered in the form of aqueous or oily solutions or suspensions, tablets, pills, gelatine capsules, syrups, drops or suppositories. Thus, for oral administration, the pharmaceutical compositions containing the compounds of this invention, are preferably tablets, pills or gelatine capsules which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or they may also contain binders, such as starches, gelatine, methylcellulose, carboxymethylcellulose, gum-arabic, tragacanth, polyvinylpyrrolidone; disaggregating agents, such as starches, alginic acid, alginates, sodium starch glycolate; effervescing mixtures, dyestuffs; sweeteners; wetting agents, such as lecithin, polysorbates, laurylsulphates; and, in general, non-toxic and pharmacologically inactive substances used in pharmaceutical formulations.

Said pharmaceutical preparations may be manufactured in known manner, for example by means of mixing, granulating, tabletting, sugar-coating, or film-coating processes.

The liquid dispersions for oral administration may be e.g. syrups, emulsions and suspensions, The syrups may contain as carrier, for example, saccharose or saccharose with glycerine and/or mannitol and/or sorbitol. The suspensions and the emulsions may contain as carrier, for example, a natural gum, agar, sodium alginate, pectin, methylcellulose, carboxymethylcellulose, or polyvinyl alcohol. The suspensions or solutions for intramuscular injections may contain together with the active compound a pharmaceutically acceptable carrier, e.g..sterile water, olive oil, sesame oil, miglyol, ethyl oleate, glycols, e.g. propylene glycol, and one or more customary ingredients according to the pharmaceutical formulation techniques, and if desired, a suitable amount of lidocaine hydrochloride. The solutions for intravenous injections or infusions may contain as carrier, for example, sterile water or preferably they may be in the form of sterile aqueous isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

Preferred compounds of formula (i), suitable for treating autoimmune diseases in mammals, including humans, are the compounds of formula (I) wherein X represents:

a) a —S(O)$_n$—group wherein n is as defined above;
b) a —CH(R$_6$)—group wherein R$_6$ represents hydrogen or C$_1$ or C$_2$-alkyl;
c) an —O—CH— or a —S(O)$_n$—CH—
　　　|　　　　　　　　|
　　　R$_6$　　　　　　R$_6$ group, wherein n and R$_6$ are as defined above; or
d) a

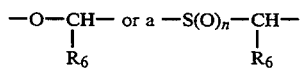

group, wherein R$_6$ is as defined above;

R$_1$ represent C$_1$–C$_4$ alkyl or phenyl, the phenyl being unsubstituted or substituted by a substituent chosen from halogen, trifluoromethyl, C$_1$–C$_6$ alkyl and C$_1$–C$_6$ alkoxy;

R$_2$ represents:
a) hydrogen, halogen, C$_1$–C$_4$ alkyl or C$_1$–C$_4$ alkoxy;
b) nitro, amino, formylamino or C$_2$–C$_4$ alkanoylamino;
c) di(C$_1$ or C$_2$ alkyl)amino or a

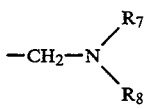

group, wherein each of R$_7$ and R$_8$ independently is C$_1$–C$_4$ alkyl or R$_7$ and R$_8$, taken together with the nitrogen atom to which they are linked, form a heterocyclic ring which is selected from N-pyrrolidinyl, N-piperazinyl, morpholino, thiomorpholino and piperidino and which is unsubstituted or substituted by C$_1$–C$_4$ alkyl;

d) —CH$_2$OH, —COOH or C$_2$–C$_7$ alkoxycarbonyl;
e) a

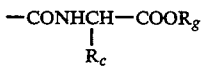

group, wherein R$_g$ is hydrogen or C$_1$–C$_4$ alkyl and R$_c$ is as defined above;

f) a —CH$_2$OCO(CH$_2$)$_n$COOR$_f$ or a —NHCO(CH$_2$)$_n$COOR$_f$ group, wherein n is as defined above and R$_f$ is hydrogen or C$_1$–C$_4$ alkyl;

g) C$_2$–C$_7$ alkoxycarbonyl substituted by a

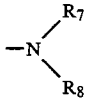

group, wherein
R$_7$ and R$_8$ are as defined above;
R$_3$ is as R$_2$ defined above under a);
Q represents hydrogen or a

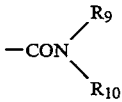

group wherein R$_9$ represents hydrogen or C$_1$–C$_6$ alkyl and R$_{10}$ represents C$_1$–C$_{10}$ alkyl, a

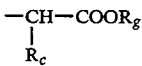

group wherein R$_c$ and R$_g$ are as defined above or a —(A′)$_m$—R$_{11}$ group wherein m is as defined above. A′ is a C$_1$–C$_3$ alkylene chain and R$_{11}$ is:

a) pyridyl, unsubstituted or substituted by a substituent chosen from halogen, $C_1$ or $C_2$ alkyl and $C_1$ or $C_2$ alkoxy;
b) phenyl, unsubstituted or substituted by one or two substituents independently chosen from halogen, $CF_3$, $C_1$-$C_4$ alkyl, $C_1$-$C_4$ alkoxy, amino, nitro, formylamino, $C_2$-$C_4$ alkanoylamino and di($C_1$-$C_4$ alkyl)amino;
c) phenyl substituted by $C_2$-$C_7$ alkoxycarbonyl or by a

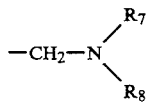

group, wherein $R_7$ and $R_8$ are as defined above, and optionally by another substituent chosen from halogen, $C_1$-$C_4$ alkyl and $C_1$-$C_4$ alkoxy;
d) 2-thienyl or 2-furyl;
e) a heterocyclic ring which is selected from 2-pyrimidyl, 2-thiazolyl and 3-isoxazolyl and which is unsubstituted or substituted by $C_1$ or $C_2$ alkyl; and the pharmaceutically acceptable salts thereof.

Further preferred compounds of formula (I) are those in which X represents:

a') a sulphur atom;
b') a

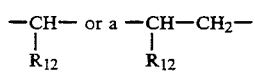

group, wherein $R_{12}$ is hydrogen or methyl; or
c') a

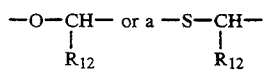

group, wherein $R_{12}$ is as defined above;
$R_1$ represents phenyl unsubstituted or substituted by a substituent chosen from halogen, trifluoromethyl and $C_1$-$C_4$-alkyl
$R_2$ represents:

a') hydrogen, halogen, $C_1$-$C_4$ alkyl, $C_1$-$C_4$ alkoxy, amino or a

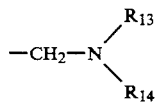

group, wherein each of $R_{13}$ and $R_{14}$ independently is $C_1$-$C_4$ alkyl or $R_{13}$ and $R_{14}$, taken together with the nitrogen atom to which they are linked, form a heterocyclic ring which is selected from N-pyrrolidinyl, N-piperazinyl, morpholino, thiomorpholino and piperidino and which is unsubstituted or substituted by methyl;
b') —COOH, $C_2$-$C_7$ alkoxycarbonyl or a

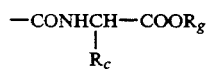

group, wherein $R_g$ is hydrogen or $C_1$-$C_4$ alkyl and $R_c$ is hydrogen, phenyl or the side-chain of an α-aminoacid;
c') a —NHCO(CH$_2$)$_n$COOR$_g$ group, wherein n is as defined above and $R_g$ is hydrogen or $C_1$-$C_4$ alkyl;
d') a $C_2$-$C_7$ alkoxycarbonyl group substituted by a

group, wherein $R_{13}$ and $R_{14}$ are as defined above;
$R_3$ represents hydrogen, halogen or $C_1$-$C_4$ alkyl;
Q represents hydrogen or a

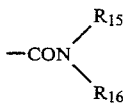

group wherein $R_{15}$ is hydrogen or $C_1$-$C_2$ alkyl and $R_{16}$ is $C_1$-$C_6$ alkyl, a

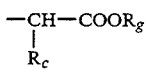

group, wherein $R_g$ is hydrogen or $C_1$-$C_4$ alkyl and $R_c$ is as defined above, or a —(A')$_m$—$R_{17}$ group wherein m is zero or 1, A' is a $C_1$-$C_3$ alkylene chain and $R_{17}$ is:

a'') unsubstituted pyridyl; or phenyl unsubstituted or substituted by a substituent chosen from halogen, $CF_3$, $C_1$-$C_2$ alkyl, $C_1$-$C_2$ alkoxy, nitro, di($C_1$-$C_2$ alkyl)amino and a

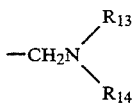

group, wherein and $R_{13}$ and $R_{14}$ are as defined above;
b'') 2-thienyl or 2-furyl; or
c'') a heterocyclic ring which is selected from 2-thiazolyl or 3-isoxazolyl and which is unsubstituted or substituted by methyl; and the pharmaceutically acceptable salts thereof. Specific examples of preferred compounds of formula (I), suitable for treating autoimmune diseases, are the following ones:

2-cyano-3-(1,4-dihydro-1-phenyl-[1]-benzothiopyrano[4,3-c]pyrazol-3-yl)-3-oxo-N-phenyl-propanamide;

N-benzyl-2-cyano-3-(1,4-dihydro-1-phenyl-[1]-benzothiopyrano[4,3-c]pyrazol-3-yl)-3-oxo-propanamide;

2-cyano-N-(4-fluoro-phenyl)-3-(1,4-dihydro-1-phenyl-[1]benzothiopyrano[4,3-c]pyrazol-3-yl)-3-oxo-propanamide;

2-cyano-N-(4-fluoro-phenyl)-3-[1-(4-fluoro-phenyl)-1,4-dihydro-[1]-benzothiopyrano[4,3-c]pyrazol-3-yl]-3-oxo-propanamide;

2-cyano-3-(1,4-dihydro-8-methyl-1-phenyl-[1]-benzothiopyrano[4,3-c]pyrazol-3-yl)-3-oxo-N-phenyl-propanamide;

3-(8-chloro-1,4-dihydro-1-phenyl-[1]-benzothiopyrano[4,3-c]pyrazol-3-yl)-2-cyano-3-oxo-N-phenyl-propanamide;

N-(3-chloro-phenyl)-2-cyano-3-(1,4-dihydro-1-phenyl-[1]benzothiopyrano[4,3-c]pyrazol-3-yl)-3-oxo-propanamide;

2-cyano-3-(1,4-dihydro-1-phenyl-indeno[1,2-c]pyrazol-3-yl)-3-oxo-N-phenyl-propanamide;

2-cyano-N-(4-fluoro-phenyl)-3-[1-(4-fluoro-phenyl)-1,4-dihydroindeno[1,2-c]pyrazol-3-yl]-3-oxo-propanamide;

2-cyano-N-(4-fluoro-phenyl)-3-(1,4-dihydro-1-phenyl-indeno[1,2-c]pyrazol-3-yl)-3-oxo-propanamide;

N-(3-chloro-phenyl)-2-cyano-3-(1,4-dihydro-1-phenyl-indeno[1,2-c]pyrazol-3-yl)-3-oxo-propanamide;

2-cyano-3-(1,4-dihydro-1-phenyl-[1]-benzopyrano[4,3-c]pyrazol-3-yl)-3-oxo-N-phenyl-propanamide;

2-cyano-3-(1,4-dihydro-7-methyl-1-phenyl-indeno[1,2-c]pyrazol-3-yl)-3-oxo-N-phenyl-propanamide;

2-(7-tert.butyl-1,4-dihydro-1-phenyl-indeno[1,2-c]pyrazol-3-yl)-2-cyano-3-oxo-N-phenyl-propanamide;

2-cyano-3-(7-fluoro-1,4-dihydro-1-phenyl-indeno[1,2-c]pyrazol-3-yl)-3-oxo-N-phenyl-propanamide;

2-cyano-N-(4-fluoro-phenyl)-3-(7-fluoro-1,4-dihydro-1-phenyl-indeno[1,2-c]pyrazol-3-yl-3-oxo-propanamide;

2-cyano-N-(4-fluoro-phenyl)-3-(1,4-dihydro-7-methyl-1-phenyl-indeno[1,2-c]pyrazol-3-yl)-3-oxo-propanamide;

3-(6-tert.butoxycarbonyl-1,4-dihydro-1-phenyl-[1]-benzothiopyrano[4,3-c]pyrazol-3-yl)-2-cyano-3-oxo-N-phenyl-propanamide;

3-(5-tert.butoxycarbonyl-1,4-dihydro-1-phenyl-indeno[1,2-c]pyrazol-3-yl)-2-cyano-3-oxo-N-phenyl-propanamide;

2-cyano-3-(1,4-dihydro-5-morpholinomethyl-1-phenyl-indeno[1,2-c]pyrazol-3-yl)-3-oxo-N-phenyl-propanamide;

2-cyano-3-(8-fluoro-1,4-dihydro-6-morpholinomethyl-1-phenyl-[1]-benzopyrano[4,3-c]pyrazol-3-yl)-3-oxo-N-phenyl-propanamide; and the pharmaceutically acceptable salts thereof, in particular the sodium and the potassium salts.

The following examples illustrate but do not limit the present invention.

EXAMPLE 1

Mycobacterium Smegmatis induced adjuvant arthritis in rats Adjuvant arthritis is induced in groups of 10–30 male Lewis rats, weighing 150 g, by injecting 75 $\mu g$ of M. Smegmatis in 50 $\mu l$ of mineral oil into the plantar surface of the right hind foot pad. The test compounds are administered at 10 mg/kg i.p.), 5 days a week for 4 weeks, starting on the same day of the mycobacterium injection. The volume of the controlateral (systematic phase) hind foot pad is measured pletismographically on days 18, 21 and 25.

Following Table 1 summarizes the test data obtained for a representative group of compounds according to the present invention, i.e. 2-cyano-3-(1,4-dihydro-1-phenyl-[1]benzothiopyrano[4,3-c]pyrazol-3-yl)-3-oxo-N-phenyl-propanamide (internal code FCE 24578), N-benzyl-2-cyano-3-(1,4-dihydro-1-phenyl-[1]-benzothiopyrano [4,3-c]pyrazol-3-yl)-3-oxo-propanamide (internal code FCE 25324) and 2-cyano-3-(4,5-dihydro-1-phenyl-[1]-benz[g]indazol-3-yl)-3-oxo-N-phenyl-propanamide (internal code FCE 25161).

TABLE 1

Activity or FCE 24578, FCE 25324 and FCE 25161 on the adjuvant arthritis in rats.
Systemic phases or the disease (left hind paw)

| Treatment | no animals | Oedema volume (mm$^3$) ± S.E. Days | | | % inhibition vs. controls Days | | |
|---|---|---|---|---|---|---|---|
| | | 18 | 21 | 25 | 18 | 21 | 25 |
| FCE 24578 10 mg/kg i.p. | 10 | 310 ± 180** | 470 ± 215** | 460 ± 241** | 75 | 65 | 68 |
| Vehicle | 30 | 1215 ± 131 | 1342 ± 135 | 1418 ± 164 | 0 | 0 | 0 |
| FCE 25324 10 mg/kg i.p. | 10 | 565 ± 72* | 575 ± 97** | 545 ± 78** | 51 | 57 | 60 |
| Vehicle | 30 | 1158 ± 132 | 1332 ± 150 | 1372 ± 152 | 0 | 0 | 0 |
| FCE 25161 10 mg/kg i.p. | 10 | 665 ± 91** | 675 ± 96** | 685 ± 93** | 50 | 49 | 49 |
| Vehicle | 30 | 1335 ± 104 | 1317 ± 77 | 1347 ± 113 | 0 | 0 | 0 |

*P 0.05 vs controls (Dunnett's "t" test)
**P 0.01

Following Table 2 summarizes the test data obtained in the same test for another representative group of compounds according to the present invention, i.e. 2-cyano-N-(4-fluoro-phenyl)-3-[1-(4-fluoro-phenyl)-1,4-dihydro-indeno[1,2-c]pyrazol-3-yl]-3-oxo-propanamide (internal code FCE 26317), 2-cyano-3-(1,4-dihydro-1-phenyl-[1]-benzopyrano[4,3-c]pyrazol-3-yl)-3-oxo-N-phenyl-propanamide (internal code FCE 25158), 2-cyano-3-(1,4-dihydro-1-phenyl-indeno[1,2-c]pyrazol-3-yl)-3-oxo-N-phenyl-propanamide (internal code FCE 25276), 3-(6-tert-butoxycarbonyl-1,4-dihydro-1-phenyl-[1]-benzothiopyrano[4,3-c]pyrazol-3-yl)-2-cyano-3-oxo-N-phenyl-propanamide (internal code FCE 26674), 2-cyano-3-(7-fluoro-1,4-dihydro-1-phenyl-indeno[1,2-c]pyrazol-3-yl)-3-oxo-N-phenyl-propanamide (internal code FCE 26676) and 2-cyano-3-(1,4-dihydro-5-morpholinomethyl-1-phenyl-indeno [1,2-c]pyrazol-3-yl)-3-oxo-N-phenyl-propanamide (internal code FCE 26626).

TABLE 2

Activity of FCE 26317, FCE 25158, FCE 25276, FCE 26674, FCE 26676 and FCE 26626 on the adjuvant arthritis in rats.
Systemic phases of the disease (left hind paw)

| Compound | dose mg/kg i.p. | no animals | Oedema volume (mm$^3$) ± S.E. Days | | | % inhibition vs. controls Days | | |
|---|---|---|---|---|---|---|---|---|
| | | | 18 | 21 | 25 | 18 | 21 | 25 |
| FCE 26317 | 10 | 7 | 629 ± 347 | 686 ± 393 | 683 ± 417 | 37 | 38 | 44 |
| FCE 25158 | 10 | 6 | 700 ± 198 | 683 ± 174 | 717 ± 182 | 30 | 38 | 41 |
| FCE 25276 | 10 | 8 | 587 ± 233 | 587 ± 254* | 512 ± 304* | 41 | 47 | 58 |
| FCE 26674 | 10 | 7 | 757 ± 209 | 662 ± 182 | 812 ± 226 | 24 | 40 | 34 |
| FCE 26676 | 10 | 8 | 350 ± 127** | 512 ± 203* | 612 ± 225* | 65 | 54 | 50 |
| FCE 26626 | 10 | 8 | 425 ± 173* | 587 ± 222* | 562 ± 234* | 57 | 47 | 54 |
| Vehicle | — | 23 | 996 ± 124 | 1104 ± 119 | 1126 ± 134 | 0 | 0 | 0 |

*P 0.05 vs controls (Student's "t" test)
**P 0.01 vs controls (student's "t" test)

The data set out in Tables 1 and 2 show clearly that a representative group of test compounds according to the present invention produces a marked inhibition of the arthritis, throughout the period of observation which lasts 25 days. Furthermore, according to the same test data, a person skilled in the art can appreciate that also the compounds, which have not been found significant in the statistical evaluation, are similarly endowed with valuable biological activity.

FORMULATION EXAMPLES

Formulation 1: Tablets

Tablets, each weighing 150 mg and containing 50 mg of the active substance are manufactured as follows:
Composition: (for 10000 tablets)

| | |
|---|---|
| 2-cyano-3-(1,4-dihydro-1-phenyl-[1]-benzothiopyrano[4,3-c]pyrazol-3-yl)-3-oxo-N-phenyl-propanamide | 500 g |
| Lactose | 710 g |
| Corn starch | 238 g |
| Talc powder | 36 g |
| Magnesium stearate | 16 g |

2-cyano-3-(1,4-dihydro-1-phenyl-[1]-benzothiopyrano [4,3-c]pyrazol-3-yl)-3-oxo-N-phenyl-propanamide, lactose and half of the corn starch are mixed; the mixture is then forced through a sieve of 0.5 mm openings. Corn starch (18 g) is suspended in warm water (180 ml). The resulting paste is used to granulate the powder. The granules are dried, comminuted on a sieve of sieve size 1.4 mm, then the remaining quantity of starch, talc and magnesium stearate is added, carefully mixed and processed into tablets using punches of 8 mm diameter.

Formulation 2: Capsules (50 mg)

| | |
|---|---|
| 2-cyano-3-(1,4-dihydro-1-phenyl-[1]-benzothiopyrano[4,3-c]pyrazol-3-yl)-3-oxo-N-phenyl-propanamide | 50 mg |
| Lactose | 298 mg |
| Corn starch | 50 mg |
| Magnesium stearate | 2 mg |
| Total | 400 mg |

Encapsulate in two-piece hard gelatin capsules.

Formulation 3: Suppository (100 mg)

| | |
|---|---|
| 2-cyano-3-(1,4-dihydro-1-phenyl-[1]-benzothiopyrano[4,3-c]pyrazol-3-yl)-3-oxo-N-phenyl-propanamide | 0.10 g |
| Lecithin | 0.07 g |
| Cocoa butter | 0.83 g |
| Total | 1.00 g |

Formulation 4: Syrup

| | |
|---|---|
| 2-cyano-3-(1,4-dihydro-1-phenyl-[1]-benzothiopyrano[4,3-c]pyrazol-3-yl)-3-oxo-N-phenyl-propanamide, Sodium salt | 1.0 g |
| Gum tragacanth | 1.0 g |
| Methyl-p-hydroxybenzoate | 0.135 g |
| Propyl-p-hydroxybenzoate | 0.015 g |
| Polyoxymethylene sorbitan monolaurate | 5 g |
| Glycerine 30 Be | 5 g |
| Saccharose | 50 g |
| Natural Flavour | q.s. |
| Purified water to make | 100 g |

Formulation 5: Cream

| | |
|---|---|
| 2-cyano-3-(1,4-dihydro-1-phenyl-[1]-benzothiopyrano[4,3-c]pyrazol-3-yl)-3-oxo-N-phenyl-propanamide | 20.0 |
| White petrolatum | 100.0 |
| Cetylstearyl alcohol | 72.0 |
| Mineral oil | 60.0 |
| Polypropylene glycol | 22.5 |
| 4-Chloro-m-cresol | 1.0 |
| Purified water to make | 1.0 g |

Formulation 6: Ointment

| | |
|---|---|
| 2-cyano-3-(1,4-dihydro-1-phenyl-[1]-benzothiopyrano[4,3-c]pyrazol-3-yl)-3-oxo-N-phenyl-propanamide | 50.0 |
| Mineral oil | 50.0 |
| Propylene glycol | 50.0 |
| Petrolatum, to make | 1.0 g |

Formulation 7: Suspension for intramuscular injection

| | |
|---|---|
| 2-cyano-3-(1,4-dihydro-1-phenyl-[1]-benzothiopyrano[4,3-c]pyrazol-3-yl)-3-oxo-N-phenyl-propanamide | 5.0 g |
| Aluminum monostearate | 2.0 g |
| Sesame oil to make | 100 ml. |

We claim:

1. A method of treating a mammal suffering from rheumatoid arthritis, which method comprises administering to said mammal a therapeutically effective amount of a heteroaryl-3-oxo-propanenitrile derivative of formula (I)

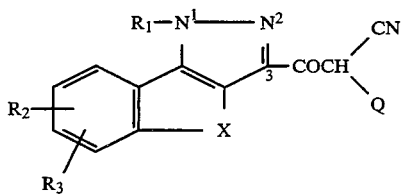

wherein

X represents a —CH(R$_4$)—group, wherein R$_4$ represents hydrogen or C$_1$-C$_6$ alkyl;

R$_1$ represents phenyl, the phenyl being unsubstituted or substituted by a substituent chosen from halogen, trifluoromethyl and C$_1$-C$_6$ alkyl;

R$_2$ represents a

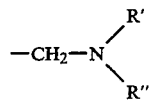

group wherein each of R' and R", taken together with the nitrogen atom to which they are linked, form a morpholino ring which is unsubstituted or substituted by C$_1$-C$_6$ alkyl;

R$_3$ is hydrogen;

Q represents a

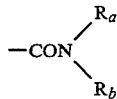

group wherein R$_a$ represents hydrogen and R$_b$ represents a —(A)$_m$—R$_5$ group wherein m is zero or 1, A is a C$_1$-C$_6$ alkylene chain and R$_5$ is phenyl, unsubstituted or substituted by one substituent chosen from halogen, CF$_3$ and C$_1$-C$_6$ alkyl; or a pharmaceutically or veterinarily acceptable salt thereof.

2. A method according to claim 1, wherein said derivative is chosen from the group consisting of 2-cyano-3-(1,4-dihydro-5-morpholinomethyl-1-phenyl-indeno-[1,2-c]pyrazol-3-yl]-3-oxo-N-phenyl propanamide;

2-cyano-3-(1,4-dihydro-7-morpholinomethyl-1-phenyl-indeno-[1,2-c]pyrazol-3-yl)-3-oxo-N-phenyl propanamide;

and the pharmaceutically and veterinarily acceptable salts thereof.

* * * * *